(12) United States Patent
Tsang et al.

(10) Patent No.: US 7,577,233 B1
(45) Date of Patent: Aug. 18, 2009

(54) ROTATING X-RAY APPARATUS FOR INSPECTION OF DEPLOYED INTRAVASCULAR DEVICES

(75) Inventors: James C. Tsang, Flanders, NJ (US); Gilbert Zweig, Morris Plains, NJ (US); Paul D. Gonzalez, Branchville, NJ (US)

(73) Assignee: Glenbrook Technologies, Inc., Randolph, NJ (US)

( * ) Notice: Subject to any disclaimer, the term of this patent is extended or adjusted under 35 U.S.C. 154(b) by 61 days.

(21) Appl. No.: 11/890,122

(22) Filed: Aug. 3, 2007

(51) Int. Cl.
*G01N 23/223* (2006.01)
*G01N 23/04* (2006.01)

(52) U.S. Cl. .............................. 378/44; 378/62; 378/207

(58) Field of Classification Search ............... 378/4, 378/15, 19, 44, 51, 62, 98, 98.2, 98.3, 98.8, 378/196, 197, 207; 250/370.08, 370.09, 250/370.11; 600/426, 429
See application file for complete search history.

(56) References Cited

U.S. PATENT DOCUMENTS

| 4,112,303 | A | * | 9/1978 | Brandt ........................ 378/17 |
| 4,896,344 | A | * | 1/1990 | Grady et al. ............... 378/98.3 |
| 5,394,455 | A | * | 2/1995 | Roeck et al. .............. 378/98.3 |
| 6,456,684 | B1 | * | 9/2002 | Mun et al. ................... 378/20 |
| 6,493,575 | B1 | * | 12/2002 | Kesten et al. ............... 600/431 |
| 6,614,871 | B1 | * | 9/2003 | Kobiki et al. ................ 378/20 |
| 6,865,254 | B2 | * | 3/2005 | Nafstadius ................... 378/65 |
| 7,426,258 | B1 | * | 9/2008 | Zweig ....................... 378/98.3 |

* cited by examiner

*Primary Examiner*—Edward J Glick
*Assistant Examiner*—Thomas R Artman
(74) *Attorney, Agent, or Firm*—Michael R. Philips

(57) ABSTRACT

The rotating X-ray apparatus disclosed has a pair of driven rotatable rings with an X-ray source mounted for impinging a beam that passes through a specimen to an X-ray receptor. A reversible motor, controlled by a reversing switch, drives the rotatable rings around the specimen. The rotatable rings are mounted between a pair of frame plates that are supported on transverse rails for lateral movement.

8 Claims, 4 Drawing Sheets

ROTATING X-RAY APPARATUS FOR INSPECTION OF DEPLOYED INTRAVASCULAR DEVICES

FIELD OF THE INVENTION

The present invention relates to the field of real-time fluoroscopic X-ray imaging, and more particularly to 180° rotating inspection of deployed intravascular devices by high resolution fluoroscopic X-ray imaging generated through the use of a low dose X-ray beam.

BACKGROUND OF THE INVENTION

Medical science has developed apparatus and processes for remediating constricted blood vessels by implanting a stent that expands a section of the blood vessel and improves blood flow. More recently, medical research has created a filter or strainer for insertion in a blood vessel, in particular the vena cava, to prevent blood clots generated after surgery from circulating and contributing to stroke or heart attack. The stent technology has been accepted medical procedure for many years, and the vascular filter is in the early stage of development and evaluation.

One form of vascular filter is a resilient three dimensional frame that may be collapsed to a narrow form in a carrier for insertion that will expand in the blood vessel when released. In contrast to the stent that hugs the blood vessel wall, the filter spreads across the lumen area within the blood vessel to strain particles from the blood stream, particularly blood clots. By catching blood clots in the filter, typically placed in the vena cava, the blood clots are prevented from causing major problems. At a calculated time after surgery, when post-surgery blood clot formation is assumed to have ceased, the filter is retrieved and the captured blood clots safely removed.

To evaluate the effectiveness of a new medical device such as a vascular filter, a considerable amount of laboratory testing must be done and results evaluated. Different materials and geometries are often compared before conducting clinical trials on animal or human subjects. Such laboratory testing involves pumping a flow of liquid, preferably blood, carrying real or simulated blood clots through a section of a blood vessel with the trial vascular filter in place and results being recorded. Useful non-human blood vessels are from pigs, having similar physiology to humans.

However, blood vessels in general, and pig blood vessels in particular, are opaque. Thus, to properly compare and evaluate the test results, the process of catching blood clots in the vascular filter being tested must be observed and documented, for example by the use of real-time fluoroscopic X-ray equipment. Real-time fluoroscopic X-ray imaging involves directing an X-ray beam through a test device to impinge onto a scintillator that converts the X-rays into energy in the visible spectrum. An advance in fluoroscopic X-ray design is disclosed in detail in U.S. patent application Ser. No. 11/606,453 filed Nov. 30, 2006. Patent application Ser. No. 11/606,453 is incorporated in its entirety herein by reference. As described therein, the fluoroscopic system produces a high resolution image while requiring only a low dose X-ray source. The present invention combines the disclosed high resolution low dose fluoroscopic system with a rotating mechanical actuator to enable non-invasive 360° examination of the vascular filter.

SUMMARY OF THE INVENTION

The rotating X-ray apparatus described herein includes a high resolution real-time fluoroscope with the X-ray source and X-ray receptor affixed at opposed positions between a pair of parallel rotatable rings. The rotatable rings are supported between a pair of frames with enclosing bearing surfaces. The supporting frames are slideably mounted on rails that allow the rotatable rings to be moved in a direction parallel to the axis of rotation of the rotatable rings. A specimen for examination is mounted on a stationary support between the X-ray source and the X-ray receptor. A drive unit is provided to rotate the rotatable rings in a first direction and reverse to rotate the rotatable rings in a second direction.

BRIEF DESCRIPTION OF THE DRAWINGS

The present invention is best understood in conjunction with the accompanying drawing figures in which like elements are identified by similar reference numerals and wherein.

DETAILED DESCRIPTION OF THE PREFERRED EMBODIMENT

Figure 1:
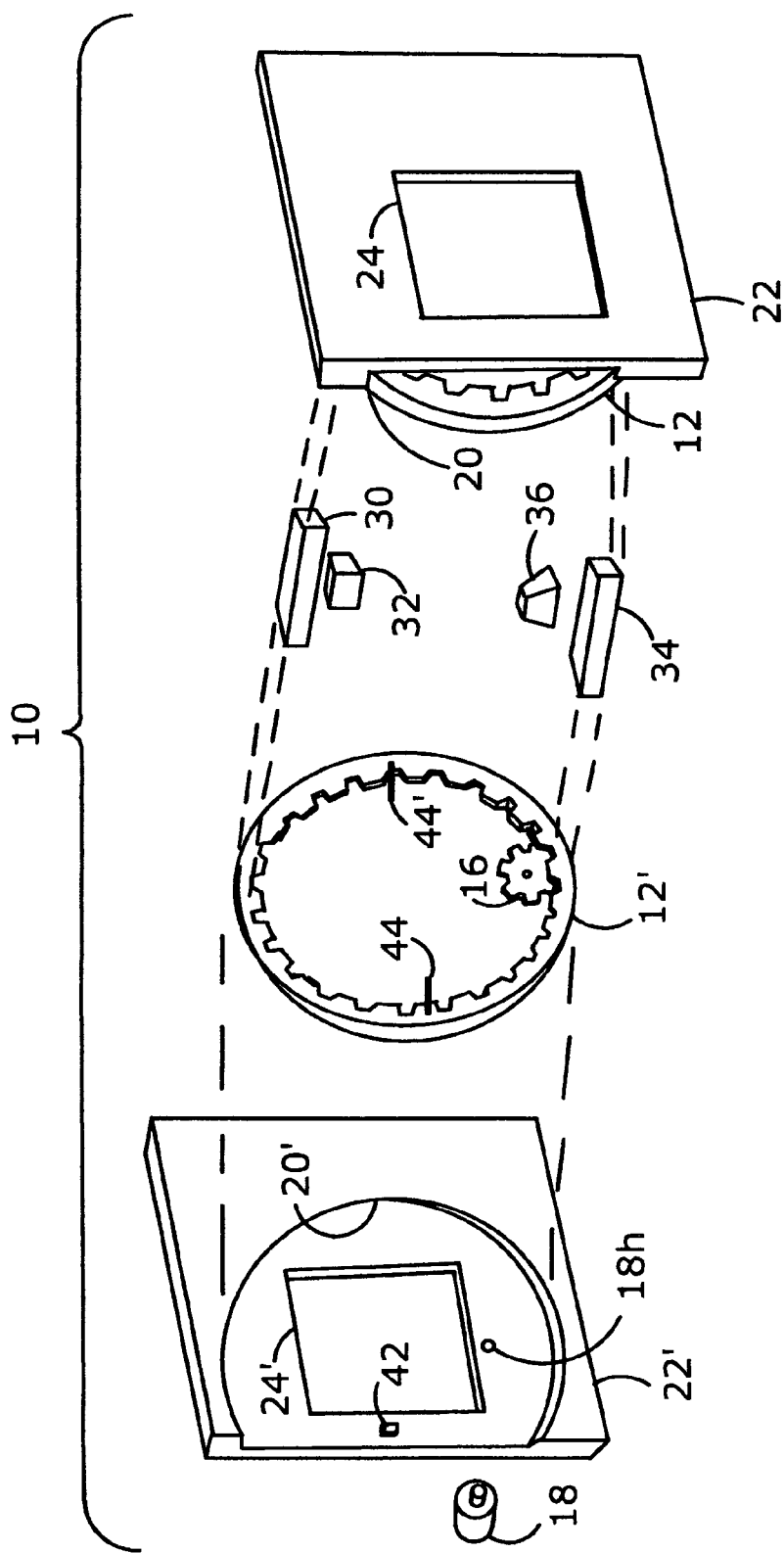
FIG. 1 is an exploded perspective view of the rotating X-ray apparatus of the present invention.

Referring now to FIG. 1, an exploded perspective view is illustrated of the rotating X-ray inspection apparatus 10 of the invention. A first plate 22 and a second plate 22' are positioned in parallel planes that are spaced apart. A window 24 is formed through plate 22 and a window 24' is formed through plate 22'. Windows 24, 24' allow a specimen to be passed therethrough for test evaluation as will be discussed below. Truncated circular tracks 20, 20' are formed in the side surfaces of plates 22, 22' in positions to circumscribe windows 24, 24' with an open edge portion of track 20' aligned with the open edge of track 20 of plate 22. Plates 22 and 22' are formed in mirror image configurations with tracks 20, 20' facing each other. Plates 22, 22' are preferably formed of a lubricous resinous material, for example a plastic resin having an integral lubricant. A preferred material for plates 22, 22' is a molybdenum filled nylon, known commercially by the trade name Nylatron.

Referring further to FIG. 1, a first ring 12 is assembled into track 20 of plate 22, and a second ring 12' is positioned for being assembled into track 20' of plate 22'. According to the preferred embodiment of the invention, rings 12, 12' are ring gears having internal teeth. A rotating means, for example a motor 18, is assembled to the outer surface of plate 22' with the shaft thereof being passed through a hole 18h, and a pinion 16 affixed thereto. Pinion 16 is in driving engagement with ring 12' in order that when motor 18 operates, ring 12' is rotated. Motor 18 is preferably a reversible electric motor able to operate in clockwise and counterclockwise directions.

Whereas ring 12' is a ring gear, alternate forms of power transmission capable of providing driven, controlled rotation are believed to be within the scope of the invention disclosed. Upon assembly, a frame is affixed to connect plate 22 to plate 22' as will be discussed below. An X-ray source support 30 is assembled between a first portion of ring 12 and a mating portion of ring 12'. X-ray source 32 is mounted to X-ray source support 30. An X-ray receptor support 34 is assembled between a second portion of ring 12 and a mating portion of ring 12'. An X-ray receptor 36 is mounted to X-ray receptor support 34. When assembled, X-ray source 32 and X-ray receptor 36 are opposed to one another. X-ray source support 30 and X-ray receptor support 34 serve to fixedly connect ring 12 to ring 12' in order that both rings 12, 12' rotate synchronously. Whereas ring 12 is preferably a ring gear for size equality with ring 12', a ring without teeth is also contemplated in place of ring 12 according to the invention. Tracks 20 and 20' are preferably formed as truncated partial circles in order to reduce the frictional drag between rings 12, 12' and plates 22, 22'.

Figure 4:
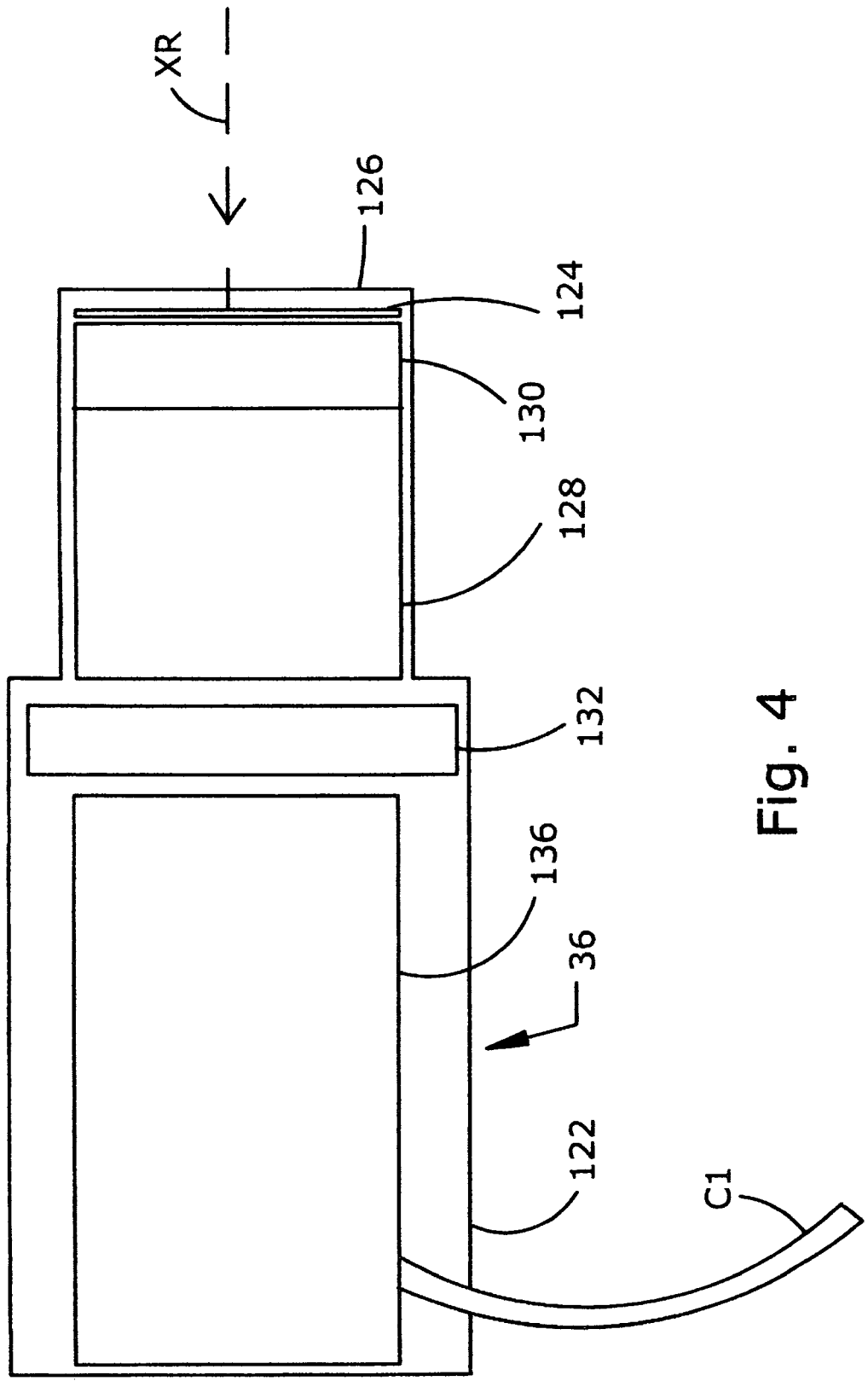
FIG. 4 is a schematic side elevation view of the X-ray receptor utilized in the present invention and as described in the patent application incorporated herein.

Referring now to FIG. 4, X-ray receptor 36 is depicted in schematic detail as in the patent application incorporated herein. A housing 122 encloses and supports the components comprising X-ray receptor 36. At least the window portion 126 of housing 122 is transparent to X-ray. X-ray beam XR passes through window portion 126 to impinge on scintillator 124, being in the form of a thin sheet or coating of radioluminescent phosphor, for example CsI or $Gd_2O_2S$. Scintillator 124 converts the impinging X-ray input radiation frequency into a visible light frequency for further processing and image projection. Scintillator 124 is positioned and maintained in intimate optical contact with the input end of a non-demagnifying image intensifier 128 to maximize transmission integrity. Scintillator 124 may be formed by directly depositing the selected phosphor on the input of image intensifier 128 or by adhering a formed phosphor sheet scintillator to the image intensifier input. Alternatively, a phosphor is deposited, or a phosphor sheet is adhered, onto a fiber optic plate or taper 130 that is in intimate optical contact with image intensifier 128. Image intensifier 128 is of the type able to increase the energy of visible light transmitted therethrough by electronic or electrostatic means while maintaining a constant image size. A specific type of non-demagnifying image intensifier that is satisfactory to the objects of the invention is known as a microchannel plate, characteristically a thin plate of conductive glass with a large number of very small apertures, on the order of 10 µm in diameter. The apertures, or microchannels, are coated to cause a single incoming light ray impacting the side wall to divide multiple times, adding photons and thus intensifying the energy level of the light ray projected therefrom. An available non-demagnifying microchannel plate image intensifier is capable of projecting an image with a resolution on the order of 25-28 lp/mm.

Referring further to FIG. 4, the intensified, non-demagnified image next passes through a close-up lens system 132 capable of focusing and transmitting the image received from proximally located image intensifier 128 to a camera 136. Camera 136 generates a video signal representing the image which is transmitted via cable C1 to an output device. Camera 136 is a compact programmable, autofocus block camera having an optical magnification multiplier of 10× and a digital zoom of 4×, equal to a total magnification capability of 40×. It is noted that optical magnification retains details and clarity to attain a desired level of resolution. A camera adequate to the requirements of the present invention is Model FCB-1X Series by Sony Corporation.

Figure 2:
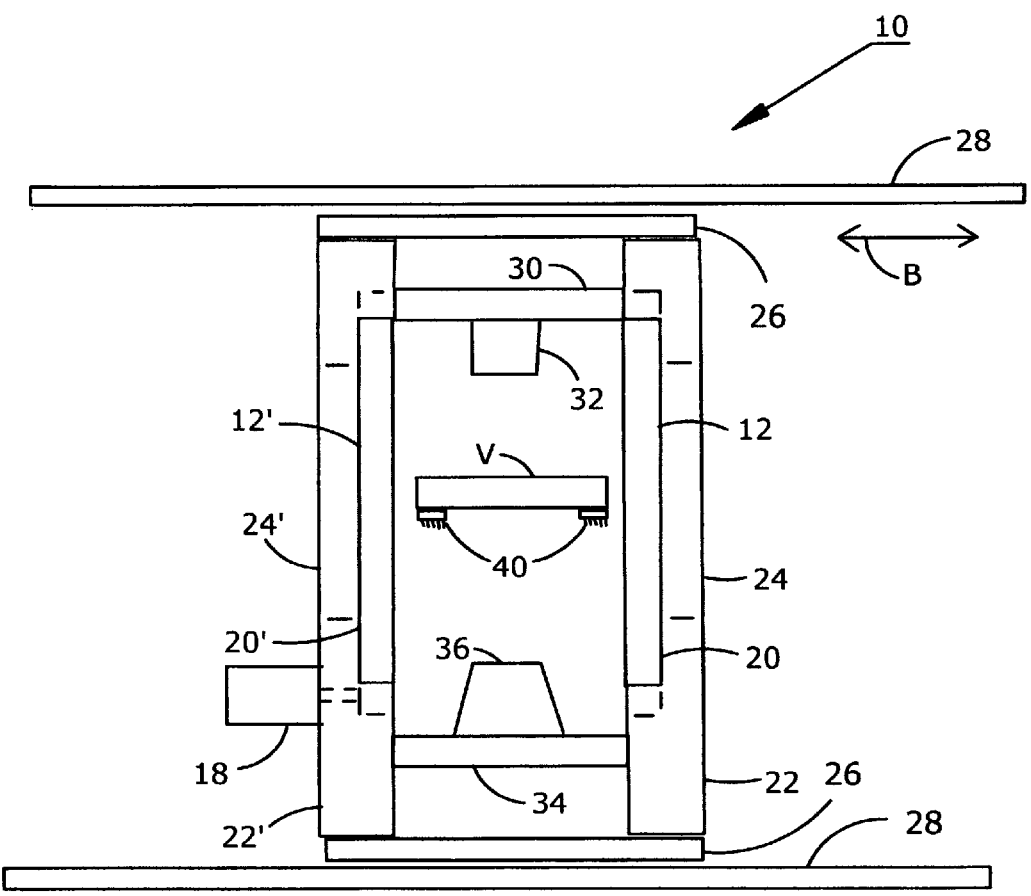
FIG. 2 is a schematic front elevation view of the apparatus of FIG. 1 in assembled condition including rails for linear movement.

Referring now to FIG. 2, an assembled front elevation view of rotating X-ray inspection apparatus 10 is shown. Ring 12 is mounted in track 20 of plate 22 in opposed relation to ring 12' mounted in track 20' of plate 22'. Ring 22 is fixedly assembled to X-ray source support 30 and X-ray receptor support 34 that are fixedly assembled to ring 22' to hold ring 22 in parallel relation with ring 22'. As assembled, X-ray source support 30 and X-ray receptor support 34 are juxtaposed to one another. X-ray source 32 and X-ray receptor 36 are mounted to respective supports 30 and 34 and are aligned with one another. X-ray source 32 and X-ray receptor 36 are substantially as described in detail in the patent application Ser. No. 11/606,453, now U.S. Pat. No. 7,426,258, incorporated herein by reference to provide a high resolution visible image from a low dose radiation beam. Plate 22 and plate 22' are assembled to one another in parallel relation by upper and lower structural frame members 26 to securely contain rings 12 and 12' in tracks 20 and 20' while allowing rings 12 and 12' to rotate freely as driven by motor 18. A pair of upper and lower rails 28 is provided to permit lateral movement of the assembled plates 22 and 22' and frame members 26 in the direction indicated by double-ended arrow B. An appropriate set of wheels, sliders or other components allow frame members 26 along with rings 12, 12' to be moved laterally as illustrated. This lateral movement may be actuated manually or mechanically, according to design and test criteria.

Referring further to FIG. 2, a specimen support 40 is fixedly mounted in the approximate center of X-ray inspection apparatus 10 with a specimen V supported thereon between X-ray source 32 and X-ray receptor 36. Specimen V is a real or simulated body part, for example being a vascular portion according to the objectives of the invention, especially a vena cava, for evaluation of blood clot filtering characteristics of an experimental filter deployed therein. Nonetheless, the novel features of the invention rotating X-ray inspection apparatus are adaptable to numerous inspection and testing regimens in medical and industrial arenas. Specimen support 40 is affixedly mounted to remain stationary within the center area of windows 24, 24' and rings 12, 12' regardless of the rotational or lateral movement of apparatus 10. During experiments for evaluating liquid flow and clot collection, an inlet hose and an outlet hose (not shown) are connected to the ends of specimen V to provide a supply of blood or other liquid. Whereas a vena cava or other body part is essentially opaque to visible light, X-ray apparatus is employed to evaluate the effectiveness of a test vascular filter.

Figure 3:
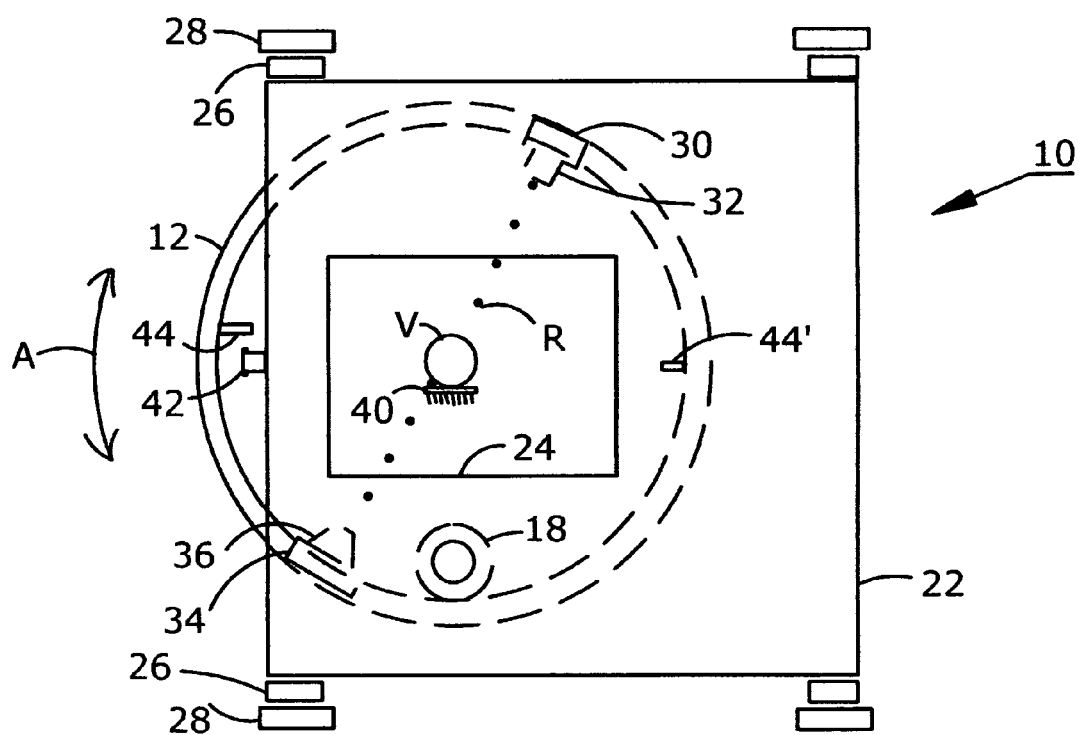
FIG. 3 is schematic side elevation view of the rotating X-ray apparatus of FIG. 2.

Referring now to FIG. 3, rotating X-ray apparatus 10 is shown in side elevation view. Specimen V is mounted on fixed specimen support 40 and is visible through window 24. Window 24 allows liquid supply hoses (not shown) to be connected to specimen V while ring 12 is rotated thereabout. An X-ray beam R passes from X-ray source 32 to X-ray receptor 36 to produce a real-time, moving image of the interior of specimen V, particularly including a vascular filter being tested in respect to filtering blood clots. Ring 12 is rotated by motor 18 in a first direction indicated by arrow A through an arc of approximately 180°, at which point a contact finger 44 actuates a switch 42, causing motor 18 and ring 12 to automatically reverse direction. Ring 12 then rotates through an arc of approximately 180° in the reverse direction until contact finger 44' actuates switch 42 and motor 18 is again caused to change direction. In this manner, invention rotating X-ray inspection apparatus 10 obtains a moving image through nearly a full 180°. In X-ray technology, a 180° rotation effectively provides a full spectrum image of the specimen. Whereas the preferred embodiment of the present invention uses a pair of fingers 44, 44' to contact switch 42 and reverse the rotation direction of rings 12, 12' every 180°, an alternate rotational configuration, e.g. a single finger 44, is considered operable to cause rings 12, 12' to reverse every approximately 350°. Whereas the preferred embodiment of the invention employs a reversing switch 42 and contact fingers 44, 44', other means of detecting the position and reversing the rotational direction of ring 12 are considered to be within the scope of the invention.

While the description above discloses preferred embodiments of the present invention, it is contemplated that numerous variations of the invention are possible and are considered to be within the scope of the claims that follow.

What is claimed is:

1. A method for evaluating an implantable device deployed in an extracorporeal blood vessel, comprising the steps of:
   a. providing a high resolution low dose fluoroscope having an X-ray source and an X-ray receptor;
   b. mounting the X-ray source and the X-ray receptor in juxtaposed positions on a rotatable apparatus;
   c. mounting an extracorporeal blood vessel that is essentially opaque to visible light and translucent to X-ray radiation, the blood vessel having an intravascular device deployed therein in a position between the X-ray source and the X-ray receptor;
   d. passing a flow of liquid carrying particles through the blood vessel and the intravascular device;
   e. rotating the rotatable apparatus; and
   f. operating the fluoroscope to evaluate the effectiveness of the intravascular device.

2. The method described in claim 1, further comprising the step of moving the high resolution low dose fluoroscope linearly in a direction parallel to an axis of the mounted body part.

3. The method described in claim 1, wherein the step of mounting the X-ray source and the X-ray receptor comprises mounting the X-ray source and the X-ray receptor on a pair of rotationally driven rings.

4. The method of claim 3, wherein the step of mounting the X-ray source and the X-ray receptor in juxtaposed positions on rotationally driven rings further comprises the step of supporting the first and second rotatable rings on a pair of mirror image bearing supports.

5. The method of claim 4, wherein the bearing supports are formed of a lubricious resin material.

6. The method of claim 1, further comprising the step of reversing the rotation of the apparatus after the rotatable apparatus has rotated through a selected arc.

7. The method described in claim 6, wherein the selected arc comprises approximately 180°.

8. The method of claim 1, wherein the step of rotating the rotatable apparatus further comprises automatically reversing the direction of rotation thereof.

* * * * *